US008581023B2

(12) United States Patent
Blake et al.

(10) Patent No.: US 8,581,023 B2
(45) Date of Patent: *Nov. 12, 2013

(54) PURPLE TRANSGENIC FLUORESCENT ORNAMENTAL FISH

(75) Inventors: Alan Blake, Austin, TX (US); Richard Crockett, Wilton, CT (US); Aidas Nasevicius, Tampa, FL (US)

(73) Assignee: Yorktown Technologies, L.P., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/561,615

(22) Filed: Jul. 30, 2012

(65) Prior Publication Data

US 2012/0317665 A1 Dec. 13, 2012

Related U.S. Application Data

(63) Continuation of application No. 13/396,382, filed on Feb. 14, 2012, now Pat. No. 8,232,450.

(60) Provisional application No. 61/443,063, filed on Feb. 15, 2011.

(51) Int. Cl.
*A01K 67/027* (2006.01)
*C12N 15/00* (2006.01)

(52) U.S. Cl.
USPC .................. 800/20; 800/13; 800/22; 800/25

(58) Field of Classification Search
USPC ........................................ 800/20, 13, 22, 25
See application file for complete search history.

(56) References Cited

U.S. PATENT DOCUMENTS

| | | | |
|---|---|---|---|
| 7,135,613 B1 | 11/2006 | Gong et al. | 800/20 |
| 7,355,095 B2 | 4/2008 | Tsai et al. | 800/25 |
| 7,700,825 B2 | 4/2010 | Blake et al. | 800/20 |
| 7,834,239 B2 | 11/2010 | Gong et al. | 800/20 |
| 8,232,450 B1 * | 7/2012 | Blake et al. | 800/20 |
| 2003/0162292 A1 | 8/2003 | Tsai et al. | 435/455 |
| 2004/0117866 A1 | 6/2004 | Tsai | 800/20 |
| 2004/0143864 A1 | 7/2004 | Gong et al. | 800/20 |
| 2005/0198701 A1 | 9/2005 | Lian et al. | 800/20 |
| 2005/0273874 A1 | 12/2005 | Tsai et al. | 800/20 |
| 2008/0052787 A1 | 2/2008 | Gong et al. | 800/20 |
| 2009/0025645 A1 * | 1/2009 | Blake et al. | 119/203 |
| 2009/0035788 A1 | 2/2009 | Griesbeck et al. | 435/7.2 |
| 2009/0133138 A1 | 5/2009 | Tsai | 800/20 |
| 2009/0255006 A1 | 10/2009 | Dougan et al. | 800/20 |
| 2010/0037331 A1 | 2/2010 | Blake et al. | 800/20 |
| 2010/0050280 A1 | 2/2010 | Blake et al. | 800/20 |
| 2010/0145889 A1 | 6/2010 | Blake et al. | 705/500 |

FOREIGN PATENT DOCUMENTS

| | | |
|---|---|---|
| EP | 2166107 | 3/2010 |
| WO | WO 00/49150 | 8/2000 |
| WO | WO 2008/022208 | 2/2008 |
| WO | WO 2009/148549 | 10/2009 |

OTHER PUBLICATIONS

Berquand et al., "Analysis of Cytoskeleton-Destabilizing Agents by Optimized Optical Navigation and AFM Force Measurements," *Microscopy Today*, 18:34-37, 2010.
Day et al., "Fluorescent protein tools for studying protein dynamics in living cells: a review," *J Biomed Opt.*, 3(3):031202, 2008.
Finley et al., "Three-color imaging using fluorescent proteins in living zebrafish embryos," *Biotechniques*, 31(1):66-70; 72, 2001.
Franco et al., "Control of initial endothelial spreading by topographic activation of focal adhesion kinase," *Soft Matter.*, 77:313-7324, 2011.
Gong et al., "Development of transgenic fish for ornamental and bioreactor by strong expression of fluorescent proteins in the skeletal muscle," *Biochem. Biophys. Res. Commun.*, 308(1):58-63, 2003.
Gong et al, "Green fluorescent protein (GFP) transgenic fish and their applications," *Genetica*, 111(1-3):213-25, 2001.
Ju et al., "Recapitulation of fast skeletal muscle development in zebrafish by transgenic expression of GFP under the *mylz2* promoter," *Dev Dyn.*, 227(1):14-26, 2003.
Laranjeira et al., "Glial cells in the mouse enteric nervous system can undergo neurogenesis in response to injury," *J Clin Invest.*, 121(9):3412-24, 2011.
Liu et al., "Development of expression vectors for transgenic fish," *Biotechnology*, 8:1268-1272, 1990.
Liu et al., "Isolation and characterization of beta-actin gene of carp (*Cyprinus carpio*)," *DNA Seq.*, 1(2):125-36, 1990.
Martynov et al., "Alternative cyclization in GFP-like proteins family," *The Journal of Biological Chemistry*, 276(24):21012-21016, 2001.
Nowotschin et al., "Live-imaging fluorescent proteins in mouse embryos: multi-dimensional, multi-spectral perspectives," *Trends in Biotechnology*, 27(5):266-276, 2009.
Parichy et al., "Zebrafish hybrids suggest genetic mechanisms for pigment pattern diversification in *Danio*," *Dev. Genes Evol.*, 211:319-328, 2001.
Shcherbo et al., "Bright far-red fluorescent protein for whole-body imaging," *Nature Methods*, 4(9):741-746, 2007.
Shkrob of al,. "Far-red fluorescent proteins evolved from a blue chromoprotein from *Actinia equina*," *Biochem. J.*, 392:649-654, 2005.
Stewart, "Go with the glow: fluorescent proteins to light transgenic organisms," *Trends Biotechnol* ., 24(4):155-62, 2006.
Subach et al., "Conversion of red fluorescent protein into a bright blue probe," *Chemistry & Biology*, 15:1116-1124, 2008.

(Continued)

*Primary Examiner* — Anoop Singh
(74) *Attorney, Agent, or Firm* — Parker Highlander PLLC

(57) ABSTRACT

The present invention relates to the method and use of fluorescent proteins in making purple transgenic fluorescent fish. Also disclosed are methods of establishing a population of such transgenic fish and methods of providing them to the ornamental fish industry for the purpose of marketing. Thus, new varieties of ornamental fish of different fluorescence colors from a novel source are developed.

11 Claims, No Drawings

(56) References Cited

OTHER PUBLICATIONS

U.S. Appl. No. 13/334,444 entitled "Chimeric Gene Constructs for Generation of Fluorescent Transgenic Ornamental Fish" by Zhiyuan Gong et al., filed Dec. 22, 2011.

Urbani, "Multi-Color approach to track *Salmonella* during infection,". University of Basel, Master's Thesis, pp. 1-35, Oct. 15, 2009.

Wan et al., "Generation of two-color transgenic zebrafish using the green and red fluorescent protein reporter genes gfp and rfp." *Mar Biotechnol* (NY), 4(2)146-54, 2002.

Zhu et al., "Regulation of the lmo2 promoter during hematopoietic and vascular development in zebrafish," *Dev. Biol.*, 281(2):256-269, 2005.

Zhu et al., "Use of the DsRed fluorescent reporter in zebrafish," *Methods Cell. Biol.*, 76:3-12, 2004.

Office Action issued in U.S. Appl. No. 13/396,382, dated Mar. 14, 2012.

Notice of Allowance issued in U.S. Appl. No. 13/396,382, dated Apr. 30, 2012.

* cited by examiner

PURPLE TRANSGENIC FLUORESCENT ORNAMENTAL FISH

This application is a continuation of application Ser. No. 13/396,382, filed Feb. 14, 2012, now U.S. Pat. No. 8,232,450, which claims priority to U.S. Provisional Application No. 61/443,063 filed on Feb. 15, 2011, the entire contents of which are specifically incorporated herein by reference without disclaimer.

BACKGROUND OF THE INVENTION

1. Field of the Invention

This invention relates to transgenic fish, particularly purple fluorescent transgenic fish.

2. Description of Related Art

Transgenic technology involves the transfer of a foreign gene into a host organism enabling the host to acquire a new and inheritable trait. The technique was first developed in mice by Gordon et al. (1980). They injected foreign DNA into fertilized eggs and found that some of the mice developed from the injected eggs retained the foreign DNA. Applying the same technique, Palmiter et al. (1982) introduced a chimeric gene containing a rat growth hormone gene under a mouse heavy metal-inducible gene promoter and generated the first batch of genetically engineered mice, which were almost twice as large as non-transgenic siblings.

In addition to the stimulation of somatic growth for increasing the gross production of animal husbandry and aquaculture, transgenic technology also has many other potential applications. First, transgenic animals can be used as bioreactors to produce commercially useful compounds by expression of a useful foreign gene in milk or in blood. Many pharmaceutically useful protein factors have been expressed in this way. For example, human 1-antitrypsin, which is commonly used to treat emphysema, has been expressed at a concentration as high as 35 mg/mL (10% of milk proteins) in the milk of transgenic sheep (Wright et al., 1991). Similarly, the transgenic technique can also be used to improve the nutritional value of milk by selectively increasing the levels of certain valuable proteins such as caseins and by supplementing certain new and useful proteins such as lysozyme for antimicrobial activity (Maga and Murray, 1995). Second, transgenic mice have been widely used in medical research, particularly in the generation of transgenic animal models for human disease studies (Lathe and Mullins, 1993). More recently, it has been proposed to use transgenic pigs as organ donors for xenotransplantation by expressing human regulators of complement activation to prevent hyperacute rejection during organ transplantation (Cozzi and White, 1995). The development of disease resistant animals has also been tested in transgenic mice (e.g. Chen et al., 1988).

Fish are also an intensive research subject of transgenic studies. There are many ways of introducing a foreign gene into fish, including: microinjection (e.g., Zhu et al., 1985; Du et al., 1992), electroporation (Powers et al., 1992), sperm-mediated gene transfer (Khoo et al., 1992; Sin et al., 1993), gene bombardment or gene gun (Zelenin et al., 1991), liposome-mediated gene transfer (Szelei et al., 1994), and the direct injection of DNA into muscle tissue (Xu et al., 1999). The first transgenic fish report was published by Zhu et al., (1985) using a chimeric gene construct consisting of a mouse metallothionein gene promoter and a human growth hormone gene. Most of the early transgenic fish studies have concentrated on growth hormone gene transfer with an aim of generating fast growing fish. While a majority of early attempts used heterologous growth hormone genes and promoters and failed to produce these fish (e.g. Chourrout et al., 1986; Penman et al., 1990; Brem et al., 1988; Gross et al., 1992), enhanced growth of transgenic fish has been demonstrated in several fish species including Atlantic salmon, several species of Pacific salmons, and loach (e.g. Du et al., 1992; Delvin et al., 1994, 1995; Tsai et al., 1995).

The zebrafish, *Danio rerio*, is a model organism for vertebrate developmental biology. As an experimental model, the zebrafish offers several major advantages such as easy availability of eggs and embryos, tissue clarity throughout embryogenesis, external development, short generation time, and easy maintenance of both the adult and the young. Transgenic zebrafish have been used as an experimental tool in zebrafish developmental biology. However, for the ornamental fish industry the dark striped pigmentation of the adult zebrafish does not aid in the efficient display of the various colors that are currently available on the market. More recently, Lamason et al. (2005) in their report showed that the Golden zebrafish carry a recessive mutation in the slc24a5 gene, a putative cation exchanger, and have diminished number, size, and density of melanosomes, which are the pigmented organelles of the melanocytes and hence are lightly pigmented as compared to the wild type zebrafish. The availability of such fish having modified pigmentation for transgenesis with fluorescent proteins would result in better products for the ornamental fish industry due to better visualization of the various colors.

Green fluorescent protein (GFP) is a useful tool in the investigation of various cellular processes. The GFP gene was isolated from the jelly-fish *Aqueous victoria*. More recently, various other new fluorescent protein genes have been isolated. For example, fluorescent proteins genes called DsRed (a red fluorescent protein gene), ZsGreen (a green fluorescent protein gene), and ZsYellow (a yellow fluorescent protein gene) have been isolated from the Anthozoa class of coral reefs (Matz et al., 1999; Wall et al., 2000). The novel fluorescent proteins encoded by these genes share 26-30% identity with GFP (Miyawaki, 2002).

Coral reef fluorescent proteins have broad application in research and development. The red fluorescent protein, DsRed, has been used as a reporter in transgenic studies involving various animal model systems: for example, filamentous fungi (Eckert et al., 2005, Mikkelsen et al., 2003); *ascidian* (Zeller et al., 2006); zebrafish (Zhu et al., 2005, Zhu and Zon, 2004, Gong et al., 2003, Finley et al., 2001); *xenopus* (Werdien et al., 2001); insect (Cho et al., 2006, Handler and Harrell, 2001, Horn et al., 2002); *drosophila* (Barolo et al., 2004); silkworm (Royer et al., 2005); mouse (Schmid et al., 2006, Vintersten et al., 2004); rat (Sato et al., 2003); and plants (Wenek et al., 2003). It has also been used as a marker in imaging studies in stem cells (Tolar et al., 2005, Long et al., 2005) and mouse (Long et al., 2005, Hadjantonakis et al., 2003). Green fluorescent protein, ZsGreen, has been used as a transformation marker in insects (Sarkar et al., 2006), knock-in mouse model for the study of KIT expressing cells (Wouters et al., 2005), and as reporters for plant transformation (Wenck et al., 2003). Yellow fluorescent protein, ZsYellow, has been used as a reporter for plant transformation (Wenck et al., 2003) and for visualizing fungal pathogens (Bourett et al., 2002).

Fluorescent proteins that produce a purple fluorescent color have also been developed. For example, the fluorescent protein called FP635 (also called TurboFP635 or Katushka) is a far-red fluorescent protein that exhibits a bright fluorescent color and is useful for visualizing living tissues (Shcherbo et al., 2007). FP635 was derived by targeted and random mutagenesis of a bright red fluorescent protein from the sea anemone *Entacmaea quadricolor* that is called eqFP578 (Shcherbo et al., 2007).

SUMMARY OF THE INVENTION

In certain embodiments, the present invention concerns making recombinant constructs and transgenic fluorescent fish and providing such fish to the ornamental fish industry.

The term "recombinant construct" is used to mean recombinant DNA constructs having sequences that do not occur in nature or exist in a form that does not occur in nature or exist in association with other materials that do not occur in nature. The term "transgenic" has historically been used in many contexts with various meanings. In the embodiments of this invention, transgenic is understood to mean that genetic material has been artificially introduced into the genome of an organism. An organism incorporating such genetic material, or progeny to which this genetic material was passed, would be considered a transgenic organism. A gene that is artificially introduced into the genome of an organism is referred to herein as a transgene.

Specific embodiments of the invention are directed to methods of making transgene. fluorescent fish having one or more chromosomally integrated expression cassettes that encode a fluorescent protein. In some embodiments, the provided fluorescent fish are fertile transgenic fluorescent fish. In a particular embodiment, the fish for use with the disclosed constructs and methods is the Golden zebrafish. Zebrafish skin color is determined by pigment cells in their skin, which contain pigment granules called melanosomes (black or brown color), xanthosomes (yellow color), erythrosomes (orange or red color), or iridosomes (iridescent colors, including white color). The number, size, and density of the pigment granules per pigment cell influence the color of the fish skin. Golden zebrafish have diminished number, size, and density of melanosomes and hence have lighter skin when compared to the wild type zebrafish. Golden zebrafish have a mutation in slc24a5 gene, rendering the fish skin lighter or less pigmented (Lamason et al., 2005).

In certain aspects, methods of making transgenic fluorescent fish are provided. Transgenic expression cassettes that may be used to make transgenic fluorescent fish may include a set of transcriptional regulatory motifs such as a promoter—which may be from the host species (herein referred to as a homologous promoter) or from another species (herein referred to as a heterologous promoter)—heterologous genes that may code for a fluorescent protein, and an appropriate RNA-processing and/or translational enhancing motif. The term "promoter" as used herein refers to the DNA elements that direct and regulate transcription. For instance, the zebrafish fast skeletal muscle myosin light chain promoter and carp β-actin promoter may be used according to the invention. In certain specific embodiments, there are provided methods to use multiple vectors or multiple copies of a transgene to express at least one fluorescent protein in order to enhance expression.

The steps involved in making the transgenic fish may also involve introduction (e.g., by injection) of the transgenic expression cassette into the zebrafish embryos or zebrafish embryonic stem cells. Embryos, fry, or fish that express the transgene may then be selected. For example, fish that express a fluorescence transgene may be selected by exposing the fish to light of appropriate wavelength and/or by visibly inspecting the fish and observing the expression of the transgene.

In certain embodiments there are provided transgenic fluorescent zebrafish comprising specific transgenic integration events. These fish are of particular interest because, for example, they embody an aesthetically pleasing level of protein fluorescence. Thus, in some specific embodiments, there is provided a transgenic zebrafish comprising a chromosomally integrated expression cassette encoding an FP635 fluorescent protein, wherein the zebrafish comprises the "Purple zebrafish 1 transformation event," sperm comprising the Purple zebrafish 1 transformation event having been deposited as ECACC accession no. 11012801. Eggs, sperm and embryos comprising these specific transgenic events are also included as part of the invention.

In certain aspects, the transgenic zebrafish comprising the Purple zebrafish 1 transformation event is further defined as a fertile, transgenic zebrafish. In other certain aspects, the transgenic zebrafish is further defined as a transgenic Golden zebrafish. The transgenic zebrafish comprising the Purple zebrafish 1 transformation event, may be homozygous or heterozygous (including, for example, hemizygous) for the integrated expression cassette. Homozygous fish bred with fish lacking an expression cassette (e.g., Golden zebrafish) will in nearly all cases produce 100% heterozygous offspring.

Transgenic fish described herein may emit far-red or purple fluorescence and hence will be unique and attractive to the ornamental fish industry. Thus, also disclosed herein are methods of providing a fluorescent transgenic zebrafish to the ornamental fish market, comprising obtaining a transgenic fish comprising the Purple zebrafish 1 transformation event, and distributing the fish to the ornamental fish market. In some embodiments, the fish are distributed by a grower to a commercial distributor. In other embodiments, the fish are distributed by a grower or a commercial distributor to a retailer for sale to the public. In one such embodiment, the fish may also be sold by the grower or commercial distributor to a regional wholesale distributor, who will then sell to a retailer for sale to the public. The retailer may be a multi-product retailer having an ornamental fish department. The fluorescent transgenic fish are also useful for the development of a biosensor system and as research models for embryonic studies such as cell lineage, cell migration, cell and nuclear transplantation, cell-cell interaction in vivo, etc.

Also provided are methods for producing a transgenic zebrafish comprising: (a) obtaining a zebrafish comprising a chromosomally integrated expression cassette encoding an FP635 fluorescent protein, wherein the zebrafish comprises the Purple zebrafish 1 transformation event, sperm comprising the Purple zebrafish 1 transformation event having been deposited as ECACC accession no. 11012801; and (b) breeding the obtained zebrafish with a second zebrafish to provide a transgenic zebrafish comprising the Purple zebrafish 1 transformation event. The second zebrafish may be a transgenic zebrafish or a non-transgenic zebrafish.

In further embodiments, also provided are methods of producing a transgenic organism, the method comprising using sperm comprising the Purple zebrafish 1 transformation, such sperm having been deposited as ECACC accession no. 11012801, to produce transgenic offspring. Such offspring may be, for example, a zebrafish, a species of the *Danio* genus, a fish species related to zebrafish, or another fish species. In some aspects, the fish may be produced using in vitro fertilization techniques known in the art or described herein.

Embodiments discussed in the context of a method and/or composition of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any embodiment of any of the present methods and compositions may consist of or consist essentially of—rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Transgenic Fish

In some aspects, the invention regards transgenic fish. Methods of making transgenic fish are described in, for example, U.S. Pat. Nos. 7,135,613; 7,700,825; 7,834,239, each of which is incorporated by reference in its entirety.

It is preferred that fish belonging to species and varieties of fish of commercial value, particularly commercial value within the ornamental fish industry, be used. Such fish include but are not limited to catfish, zebrafish, medaka, carp, tilapia, goldfish, tetras, barbs, sharks (family cyprinidae), angelfish, loach, koi, glassfish, catfish, discus, eel, tetra, goby, gourami, guppy, Xiphophorus, hatchet fish, Molly fish, or pangasius. A particular fish for use in the context of the invention is zebrafish, *Danio rerio*. Zebrafish are increasingly popular ornamental animals and would be of added commercial value in various colors. Zebrafish embryos are easily accessible and nearly transparent. A fish that is of particular use with the disclosed constructs and methods is the Golden Zebrafish. Zebrafish skin color is determined by pigment cells in their skin, which contain pigment granules called melanosomes. The number, size, and density of the melanosomes per pigment cell influence the color of the fish skin. Golden zebrafish have diminished number, size, and density of melanosomes and hence have lighter skin when compared to the wild type zebrafish. Golden zebrafish have a mutation in the slc24a5 gene, which codes for a putative cation exchanger localized to intracellular membrane, thus rendering the fish skin lighter or less pigmented (Lamason et al., 2005).

Fertilization from Frozen Sperm

Fish sperm freezing methods are well-known in the art; see, e.g., Walker and Streisinger (1983) and Draper and Moens (2007), both of which are incorporated herein by reference in their entireties. To obtain transgenic fish disclosed herein, frozen zebrafish sperm may be used to fertilize eggs, as described in Draper and Moens (2007).

Eggs are collected as described in Draper and Moens (2007). Briefly, two females are placed in tricaine solution at 16 mg/100 mL water. After gill movement has slowed, one of the fish is removed and rinsed in water. The fish is placed on a paper towel to dry briefly and then transferred to a small plastic dish. With slightly damp fingers, one finger is placed on the dorsal side of the fish. The eggs are removed by gently pressing on the ventral side of the fish, starting just behind the pectoral fins and moving toward the tail.

The eggs from the female zebrafish are squeezed into a 35 mm plastic Petri dish. The sperm are thawed at 33° C. in a water bath for 8-10 sec. 70 µl room temperature Hanks solution is added to the vial and mixed. The eggs are then immediately added to the vial and gently mixed. The sperm and eggs are activated by adding 750 µl of fish water and mixing. The mixture is incubated for 5 min at room temperature. The dish is then filled with fish water and incubated at 28° C. After 2-3 hrs, fertile embryos are transferred to small dishes where they are further cultured.

Parichy and Johnson, 2001, which is incorporated by reference in its entirety, provides additional examples regarding in vitro fertilization.

The invention further encompasses progeny of a transgenic fish containing the Purple zebrafish 1 integration event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The hybrid progeny of these matings have the benefits of the transgene for fluorescence combined with the benefits derived from these other lineages.

The simplest way to identify fish containing the Purple zebrafish 1 transformation event is by visual inspection, as the fish in question would be purple colored and immediately distinguishable from non-transgenic fish.

EXAMPLES

The invention will now be further described with reference to the following examples. These examples are intended to be merely illustrative of the invention and are not intended to limit or restrict the scope of the invention in any way and should not be construed as providing conditions, parameters, reagents, or starting materials that must be utilized exclusively in order to practice the art of the present invention.

Example 1

Purple Transgenic Zebrafish

Transgenic fish exhibiting a purple color are provided. The FP635 fluorescent protein open reading frame was acquired from Evrogen, JSC as the pTurboFP635-N plasmid, which is commercially available (Cat. No. FP722). This protein was derived from TurboRFP, which is a modified version of the red fluorescent protein eqFP578 from *Entacmaea quadricolor*. The FP635 protein was introduced into an expression cassette. The expression cassette sequence was verified using restriction endonucleases and by sequencing of the completed cassette. To make the transgenic fish, the constructs were purified by conventional methods and introduced into founder fish.

The specific transgenic events embodied in these fish are designated Purple zebrafish 1. Sperm from these fish may be used to fertilize zebrafish eggs, using methods known to those of ordinary skill in the art and methods described herein, and thereby breed transgenic zebrafish that comprise these specific transgenic integration events. Sperm from this line is deposited at the European Collection of Cell Cultures (ECACC), Porton Down, Salisbury, SP4 0JG, United Kingdom, on Jan. 28, 2011, under the provisions of the Budapest Treaty as "Purple zebrafish 1" (accession no. 11012801; cell line ZEBRAFISH 2011.1 PZF001).

The fluorescent transgenic fish have use as ornamental fish in the market. Stably expressing transgenic lines can be developed by breeding a transgenic individual with a wild-type fish, mutant fish, or another transgenic fish. The desired transgenic fish can be distinguished from non-transgenic fish by observing the fish in white light, sunlight, ultraviolet light, blue light, or any other useful lighting condition that allows visualization of the purple color of the transgenic fish.

The fluorescent transgenic fish should also be valuable in the market for scientific research tools because they can be used for embryonic studies such as tracing cell lineage and cell migration. Additionally, these fish can be used to mark cells in genetic mosaic experiments and in fish cancer models.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

U.S. Pat. No. 7,135,613
U.S. Pat. No. 7,700,825
U.S. Pat. No. 7,834,239
Barolo et al., *Biotechniques*, 36(3):436-440; 442, 2004.
Bourett et al., *Fungal Genet. Biol.*, 37(3):211-220, 2002.
Brem et al., *Aquaculture*, 68:209-219, 1988.
Chen et al., *J. Virol.*, 62:3883-3887, 1988.
Cho et al., *Insect. Biochem. Mol. Biol.*, 36(4):273-281, 2006.
Chourrout et al., *Aquaculture*, 51:143-150, 1986.
Cozzi and White, *Nat. Med.*, 1(9):964-966, 1995.
Delvin et al., *Can. J. Fisheries Aqua. Sci.*, 52:1376-1384, 1995.
Delvin et al., *Nature*, 371:209-210, 1994.
Draper and Moens, In: The Zebrafish Book, 5$^{th}$ Ed., Eugene, University of Oregon Press, 2007.
Du et al., *Bio/Technology*, 10:176-181, 1992.
Eckert et al., *FEMS Microbiol. Lett.*, 253(1):67-74, 2005.
Finley et al., *Biotechniques*, 31(1):66-70; 72, 2001.
Gong et al., *Biochem. Biophys. Res. Commun.*, 308(1):58-63, 2003.
Gordon et al., *Proc. Natl. Acad. Sci. USA*, 77:7380-7384, 1980.
Gross et al., *Aquaculature*, 103:253-273, 1992.
Hadjantonakis et al., *Nat. Rev. Genet.*, 4(8):613-625, 2003.
Handler and Harrell, *Biotechniques*, 31(4):820; 824-828, 2001.
Horn et al., *Insect. Biochem. Mol. Biol.*, 32(10):1221-1235, 2002.
Khoo et al., *Aquaculture*, 107:1-19, 1992.
Lamason et al., *Science*, 310(5755):1782-1786, 2005.
Lathe and Mullins, *Transgenic Res.*, 2(5):286-299, 1993.
Long et al., *BMC Biotechnol.*, 5:20, 2005.
Maga and Murray, *Biotechnology*, 13(13):1452-1457, 1995.
Matz et al., *Nat. Biotechnol.*, 17:969-973, 1999.
Mikkelsen et al., *FEMS Microbiol. Lett.*, 223(1):135-139, 2003.
Miyawaki, *Cell Struct. Funct.*, 27(5):343-347, 2002.
Palmiter et al., *Nature*, 300:611-615, 1982.
Parichy and Johnson, *Dev. Gene Evol.*, 211:319-328, 2001.
Penman et al., *Aquaculture*, 85:35-50, 1990.
Powers et al., *Mol. Marine Biol. Biotechnol.*, 1:301-308, 1992.
Royer et al., *Transfenic Res.*, 14(4):463-472, 2005.
Sarkar et al., *BMC Biotechnol.*, 6(1):27, 2006.
Sato et al., *Biochem. Biophys. Res. Commun.*, 311(2):478-481, 2003.
Schmid et al., *Glia.*, 53(4):345-351, 2006.
Shcherbo et al., *Nature Methods*, 4(9):77, 2007.
Sin et al., *Aquaculature*, 117:57-69, 1993.
Szelei et al., *Transgenic Res.*, 3:116-119, 1994.
Tolar et al., *Mol. Ther.*, 12(1):42-48, 2005.
Tsai et al., *Can. J. Fish Aquat. Sci.*, 52:776-787, 1995.
Vintersten et al., *Genesis*, 40(4):241-246, 2004.
Walker and Streisinger, *Genetics* 103: 125-136, 1983.
Wall et al., *Nat. Struct. Biol.*, 7(12):1133-1138, 2000.
Wenck et al., *Plant Cell Rep.*, 22(4):244-251, 2003.
Werdien et al., *Nucleic Acids Res.*, 29(11):E53-3, 2001.
Wouters et al., *Physiol. Genomics*, 2(3):412-421, 2005.
Wright et al., *Biotechnology*, 9:830-834, 1991.
Xu et al., *DNA Cell Biol.*, 18, 85-95, 1999.
Zelenin et al., *FEBS Lett.*, 287(1-2):118-120, 1991.
Zeller et al., *Dev. Dyn.*, 235(2):456-467, 2006.
Zhu and Zon, *Methods Cell Biol.*, 76:3-12, 2004.
Zhu et al., *Dev. Biol.*, 281(2):256-269, 2005.
Zhu et al., *Z. Angew. Ichthyol.*, 1:31-34, 1985.

What is claimed is:

1. A fluorescent progeny fish of a transgenic fluorescent zebrafish that comprises a chromosomally integrated expression cassette encoding an FP635 fluorescent protein, wherein the zebrafish and progeny both exhibit fluorescence and comprise the Purple zebrafish 1 transformation event, sperm comprising the Purple zebrafish 1 transformation event having been deposited as ECACC accession no. 11012801.

2. The progeny fish of claim 1, further defined as a fertile, transgenic zebrafish.

3. The progeny fish of claim 1, further defined as a transgenic Golden zebrafish.

4. The progeny fish of claim 1, wherein the fish is homozygous for the integrated expression cassette.

5. The progeny fish of claim 1, wherein the fish is heterozygous for the integrated expression cassette.

6. A method of providing a transgenic fish that exhibits a fluorescence to the ornamental fish market, comprising obtaining a transgenic fluorescent progeny fish in accordance with claim 1; and distributing the fish to the ornamental fish market.

7. The method of claim 6, wherein the fish are distributed by a grower to a commercial distributor.

8. The method of claim 6, wherein the fish are distributed by a grower or a commercial distributor to a retailer.

9. The method of claim 8, wherein the retailer is a multi-product retailer having an ornamental fish department.

10. A method of producing a transgenic fish that exhibits a fluorescence comprising:
  (a) obtaining a transgenic fluorescent zebrafish that exhibits a fluorescence and comprises a chromosomally integrated expression cassette encoding an FP635 fluorescent protein, wherein the zebrafish comprises the Purple zebrafish 1 transformation event, sperm comprising the Purple zebrafish 1 transformation event having been deposited as ECACC accession no. 11012801; and
  (b) breeding the obtained zebrafish with a second fish to provide a transgenic fluorescent progeny fish comprising the Purple zebrafish 1 transformation event.

11. The method of claim 10, wherein the second fish is a non-transgenic fish.

* * * * *